(12) United States Patent
Coltrera

(10) Patent No.: US 7,451,315 B2
(45) Date of Patent: Nov. 11, 2008

(54) COORDINATING, AUDITING, AND CONTROLLING MULTI-SITE DATA COLLECTION WITHOUT SHARING SENSITIVE DATA

(75) Inventor: Marc D. Coltrera, Seattle, WA (US)

(73) Assignee: University of Washington, Seattle, WA (US)

( * ) Notice: Subject to any disclaimer, the term of this patent is extended or adjusted under 35 U.S.C. 154(b) by 701 days.

(21) Appl. No.: 10/849,681

(22) Filed: May 19, 2004

(65) Prior Publication Data

US 2004/0236748 A1 Nov. 25, 2004

Related U.S. Application Data

(60) Provisional application No. 60/472,991, filed on May 23, 2003.

(51) Int. Cl.
*H04L 9/12* (2006.01)
(52) U.S. Cl. ................... 713/170; 705/2; 705/3; 705/51; 707/9; 713/180; 713/181; 726/30

(58) Field of Classification Search ............... 705/2, 705/3, 51; 707/9; 713/170, 180, 181; 726/30
See application file for complete search history.

(56) References Cited

U.S. PATENT DOCUMENTS

| 5,956,400 | A  | * | 9/1999 | Chaum et al. ............... 713/167 |
| 6,272,506 | B1 | * | 8/2001 | Bell ............................ 715/507 |
| 6,591,250 | B1 | * | 7/2003 | Johnson et al. ............... 705/51 |
| 6,912,317 | B1 | * | 6/2005 | Barnes et al. ............... 382/239 |

* cited by examiner

*Primary Examiner*—KimYen Vu
*Assistant Examiner*—Edward Zee
(74) *Attorney, Agent, or Firm*—Ronald M. Anderson

(57) ABSTRACT

Data input from multiple sites are collected and shared, using identifiers to maintain a link to sensitive portions of the data that were collected, without initially sharing the sensitive data. Unique record identifiers and parsed structure data information (PSD-Info) are used in connection with a checksum when sharing information without disclosing all of the sensitive data. Any shared subset data and the PSD-Info are encrypted with a private key and transmitted to a data recipient, who decrypts the information with a public key, verifying the identity of the sender. If later agreed by the parties, the sensitive data can be similarly transmitted. Maintaining a link between the shared information and the sensitive data that are withheld for confidential and privacy reasons provides proof for audit purposes, without disclosing the withheld data.

44 Claims, 3 Drawing Sheets

COORDINATING, AUDITING, AND CONTROLLING MULTI-SITE DATA COLLECTION WITHOUT SHARING SENSITIVE DATA

RELATED APPLICATIONS

This application is based on a provisional patent application Ser. No. 60/472,991, which was filed on May 23, 2003, the benefit in the filing date of which is hereby claimed under 35 U.S.C. § 119(e).

FIELD OF THE INVENTION

This invention generally relates to a method and system for creating and maintaining a centralized data store using data contributed by a plurality of sources, so that information embodied in the data can be accessed without requiring sharing of the sensitive data, and more specifically, pertains to a method and system enabling contributors to maintain their own data and share the information provided therein in a controlled manner, so that certain sensitive or confidential details relating to the information are maintained for purposes of auditing, but need not be disclosed to a recipient of the information.

BACKGROUND OF THE INVENTION

Two or more parties can agree to share data for a variety of purposes. In its simplest form, this agreement may include a data contributor and a data receiver. In many cases, the data that are shared will be a subset of a larger data set. An initial agreement may be reached between the parties to share a data subset, with the understanding that at some time in the future, it may be necessary to share the larger data set with the data recipient(s), contingent upon the results of analyzing the original data subset. These terms in the agreement may be necessary for temporal reasons, as well as for proprietary reasons.

For example, it may be necessary to share an initial subset of data for temporal reasons in a clinical medical trial where patient data are accumulated over the course of years. An agreement at the beginning of the trial might cover the sharing of a drug treatment outcome (e.g., decreased blood pressure), while additional data (e.g., the extent of blood pressure decrease in women vs. men, or drug side effects) may only be requested after the initial data are analyzed by the data recipient. Privacy regulations such as the Health Insurance Portability and Accessibility Act (HIPAA) strictly control the type of demographic data, which might comprise a patient's right to privacy, that can be shared in such studies. In effect, to comply with such rules, all of the clinical data collected and shared becomes a subset of a larger data set that includes the unshared demographic data. For audit purposes, the shared data must be traceable back to the unshared demographic data when required to substantiate the results of a clinical study.

An example of sharing an initial subset of data for proprietary reasons might arise if a Company B is negotiating for the purchase of an asset from a competitor, Company A. To arrive at a bid, Company B will want to know the gross sales and net profit generated by the asset. In addition, Company B will ultimately want proof of the gross sales and net profit numbers for Company A. In good faith, Company A will supply the proof once the deal is agreed to by the parties, but not before, since prematurely supplying the proof would give away valuable customer information to a competitor, which may decide not to buy the asset.

In each of these examples, data that are not being shared initially are potentially subject to tampering, substitution, and loss before the data can later be accessed during an audit or to provide proof of certain facts. To guard against these problems, the classic paradigm has been to require that all data be sent for storage to a central repository (the data receiver) at the time the data are collected. If the data are to be maintained by the data contributor, the data receiver must: (a) verify that the data actually exist at the data contributor's location; (b) ascertain that the data have not been tampered with during the time that the data contributor is the only one who has control over the data; (c) guarantee that no one else can masquerade as the data contributor during the time period when the data contributor is collecting and maintaining data; and (d) create an audit trail for unshared data, which can be traced back to the data contributor after the data are shared. Currently, the prior art does not provide an integral software tool that permits these functions to be efficiently carried out. Such a tool and the method that it implements would find use in a wide variety of applications.

SUMMARY OF THE INVENTION

To address the issues discussed above, one aspect of the present invention is thus directed to a method used when sharing data, to enable verification of data integrity. In this method, it is assumed that at least part of the data will initially be shared with another party. The data are arranged into structured components, such as records, each structured component including a plurality of sub-components, such as fields. The method begins by assigning a unique identifier to each structured component of the data, if not already assigned within the data. At least one descriptive value, e.g., a checksum, is determined for each structured component of the data to be shared. The descriptive value is determined by processing the data to be shared with a polynomial expression. The data information includes several parameters, including either the sub-components of the data to be shared, or their order, the unique identifiers assigned to the structured components of the data to be shared, and the one or more descriptive values for the data to be shared. The data information are then encrypted, producing encrypted data information that is conveyed to the party. The recipient is enabled to decrypt the encrypted data information to recover the data information, which is then stored for use in verifying the integrity of the data actually shared with the party.

In some cases, it will be necessary to determine a descriptive value for each sub-component of the data to be shared, producing a plurality of descriptive values that are included in the data information that is encrypted. In other cases, only a single descriptive value may be necessary.

The method further includes the steps of parsing the data, producing parsed structured data, and converting the parsed structured data to a platform independent format. It may also be necessary to pad the parsed structured data with a defined bit pattern. If so, the defined bit pattern is also conveyed to the party for use in subsequently verifying the integrity of the data.

The step of encrypting preferably includes the steps of providing a public key and a private key for encrypting the data information, and separately conveying the public key to the party for use in decrypting the encrypted data information. If the step of decrypting the encrypted data information with the public key is successful, the party will have verified the source of the encrypted data information, since a third party should not have the private key that was used to encrypt the data information.

At a different time, the method further includes the step of encrypting the data to be shared and the data information, producing encrypted shared data. The encrypted shared data are then conveyed to the party, who is enabled to decrypt the encrypted shared data. Thus, the data actually shared and the data information are recovered. Next, the party receiving the data actually shared verifies its integrity. To verify the integrity of the data, the method provides for determining at least one test descriptive value for each structured component of the data actually shared, by processing the data actually shared using the polynomial expression, producing test data information. If the test data information equals the data information that was previously stored, the integrity of the data actually shared is verified.

The step of determining at least one test descriptive value preferably comprises the step of parsing the data that were actually conveyed, producing parsed conveyed structured data. The parsed conveyed structured data are then converted to a platform independent format.

When determining the at least one test descriptive value, the defined bit pattern is used in padding the data actually shared.

Another aspect of the present invention is directed to a memory medium that stores machine executable instructions for carrying out the steps of the method. Still another aspect of this invention is directed to a system for ensuring verification of data integrity when sharing data like that discussed above. The system includes a memory in which machine instructions are stored, a data store providing a non-volatile storage for the data, and a processor that is coupled in communication with the memory and the data store. The processor executes the machine instructions stored in the memory, causing the processor to carry out a plurality of functions that are generally consistent with the steps of the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Exemplary System for Implementing Present Invention

The following description illustrates an exemplary application of the present invention in handling contributing, maintaining, and controlling access to information included within clinical trial data, but the invention is clearly not limited to that application.

Figure 1:
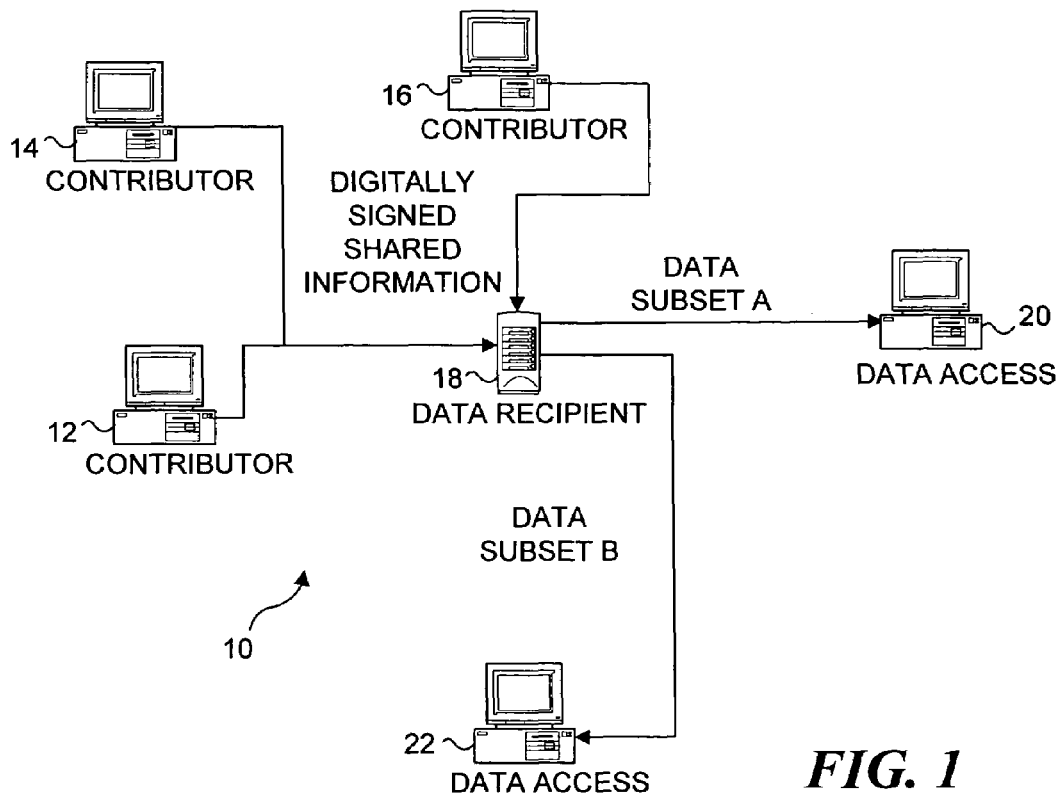
FIG. 1 is a schematic diagram of an exemplary simple network over which the present invention can be implemented.

A simplified network 10 showing how the present invention enables controlled, secure access to the information store is illustrated in FIG. 1. Network 10 may be a local area network (LAN), a wide area network (WAN), or more likely, will be a public network, such as the Internet. In this simple example, three contributors 12, 14, and 16 contribute data, such as clinical trial data that are digitally signed and may be encrypted, to a centralized data recipient 18 over network 10. The use of a digital signature to submit the data enables the data recipient to ensure the identity of the contributor submitting data. As explained below, the data may be associated with specific sensitive information known by the contributor, but at least not initially needed by a party 20 or a party 22 allowed access to shared information, such as demographic data or data identifying any specific patient participating in a clinical trial. However, it will be necessary to retain the association between the sensitive information and the information that is shared for purposes of a subsequent audit, or to provide other proof that may later be required to substantiate the reliability or authenticity of the shared information. Details explaining how selected information is shared and related details subsequently verified for audit or proof purposes are explained below.

The present invention also enables selected subsets of the data to be shared with specific parties. For example, as shown in this FIG. 1, party 20 is enabled to access a data subset A, while party 22 can access a data subset B, which may have different information than data subset A.

Figure 2:
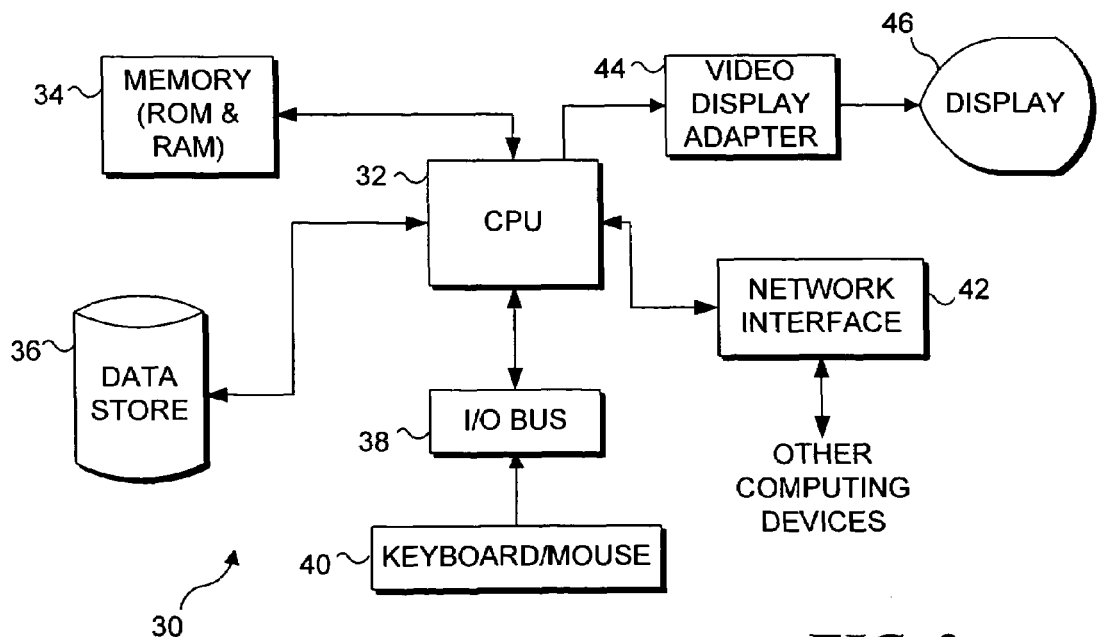
FIG. 2 is a functional block diagram of a generally conventional computing device, such as a personal computer (PC), which is suitable for implementing the functions of either a data contributor or a data recipient, in connection with the present invention.

FIG. 2 illustrates components of a generally conventional PC 30 (or other general purpose computing device) that is suitable for performing either the role of the contributor of shared information, or the recipient of the shared information. PC 30 includes a central processing unit (CPU) 32, a system memory 34, which includes both read only memory (ROM) and random access memory (RAM), and a data store 36. The components of PC 30 are coupled in communication through a motherboard or data bus (not shown), as is well known in the art. While not specifically shown, it will be understood that data store 36 can comprise a hard drive for reading from and writing to a hard disk, a magnetic drive, an optical disk drive for reading from or writing to a removable optical disk, or other form of non-volatile memory for computer readable machine instructions, data structures, program modules, and other data, some of which may comprise machine instructions that are executed for carrying out the present invention.

An input/output (I/O) bus 38 is coupled to CPU 32 and serves as an interface for one or more data ports such as serial ports, parallel ports, universal serial bus (USB) ports, and/or a personal system/2 (PS/2) port. Indeed, a keyboard and mouse 40 are connected to I/O bus 38, for input of alphanumeric characters, and for controlling and selecting items in the manner typically done with a mouse or other type of pointing device. A network interface 42 is coupled to CPU 32 to provide connection to other PCs or computing devices over network 10 and may comprise a conventional network interface device for use on a LAN, or may include a modem, or other means such as a cable modem, Digital Subscriber Line (DSL) interface, or an Integrated Service Digital Network (ISDN) interface for establishing communications over the Internet (none of which are separately shown) or over some other form of LAN or WAN. The modem, which is coupled to the CPU, may be internal or external, and may alternatively be connected to the CPU through I/O bus 38. A video display adapter 44 drives a display 46.

Sharing of Data "Information" so as to Enable Future Verification

Figure 3:
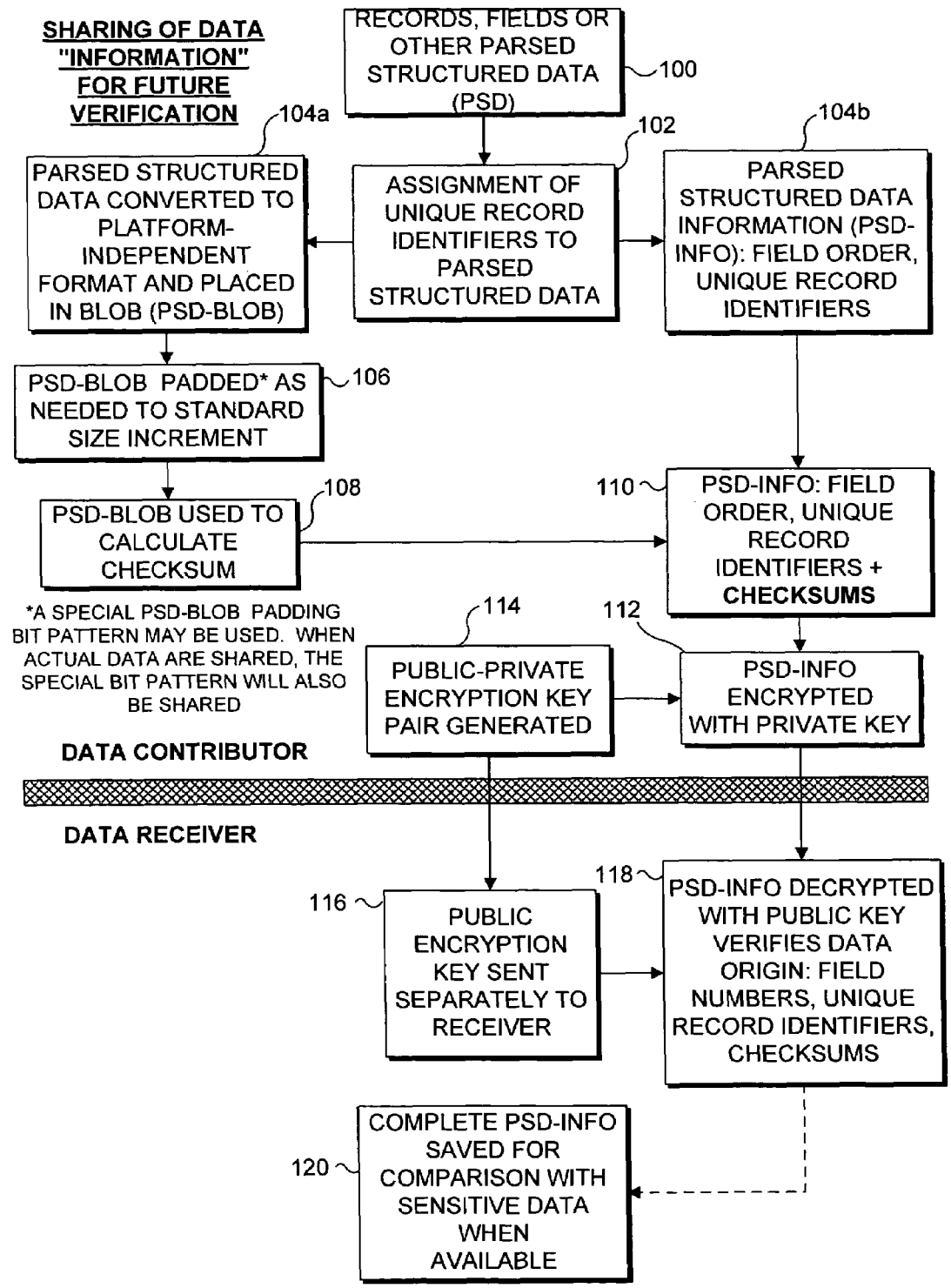
FIG. 3 is a flow chart showing the logical steps for sharing information that is subject to later verification, in accord with the present invention.

There are several important steps in a preferred implementation of the present invention. These steps include the unique identification of parsed structured data, a checksum analysis of the parsed structured data combined with the unique identifiers, and use of public-private key encryption of shared data and "information." As shown in FIG. 3, initial steps in this process are performed by a data contributor. As indicated in a step 100, parsed structured data are assembled, and the data are uniquely identified in a step 102. The data would typically include a plurality of database records. The following Table 1 shows exemplary fields for a few records of such data that might be submitted in regard to clinical trials involving a specific patient.

TABLE 1

| Field # | Field Name | Field Type | Example of the data |
|---|---|---|---|
| 1 | Subject_ID | Long integer | 10023478 |
| ... | ... | ... | ... |
| 5 | Tumor_No | Long integer | 3432212223 |
| 6 | Age | Integer | 43 |
| 7 | Gender | String | "Male" |
| 8 | Tumor type | Text | "Squamous Cell Carcinoma" |
| 9 | Primary Site | String | "Oral Cavity" |
| 10 | Photograph | PICT | 104,373 bytes |
| ... | ... | ... | ... |

In this example, information will be shared for fields 1, 5, 9, 16, 17, 18, without sharing confidential data for this patient that would violate the patient's privacy. This information will be placed in a document referred to as the parsed structured data-information (PSD-info) document. The PSD-Info initially consists of the shared field numbers (or field order) and the two unique identifiers, Subject_ID and Tumor_No, for each record, as indicated in a step 104b.

As noted in a step 104a, the shared fields that include the unique identifiers are placed in a contiguous binary large object (BLOB) for further manipulation. This object will be referred to as the PSD-Blob in the text below. The PSD-Blob is simply a string of 0s and 1s in a binary bit pattern. Using a standard mathematical polynomial formula, this pattern of binary bits can be analyzed and reduced to a single descriptive long integer called a checksum. Changing the number of bits or their order will result in a different checksum calculation result. The standard checksum polynomial employed can generate 4294967296 unique results, so the odds that two binary bit patterns will result in the same checksum are extremely unlikely (1 in 4294967296). Even if two PSD records shared the same checksum, their underlying bit patterns are guaranteed to be different because each of the PSD records has been uniquely identified, and the unique identifiers, numbers in this example, are part of their respective PSD-Blobs.

To maintain computer platform independence, differences in the way certain data types are handled must be accounted for within the PSD-Blob. For example, in the standard integer decimal number, 1234, "1" is the most significant numeral in the thousands' place on the left while "4" is the least significant numeral in the ones' place on the right. In similar fashion, a long integer is a binary number consisting of four 8-bit bytes. There is a most significant byte (MSB) and a least significant byte (LSB). The order of MSB-to-LSB can be either left-to-right or right-to-left depending on the computer platform (Windows™, Macintosh™, UNIX™, etc). The order used will change the binary bit pattern and hence, the checksum calculation, if the data contributor and the data receiver are on different platforms. To guarantee platform independence, all such data types in the PSD-Blob are converted to a standardized format prior to checksum calculation.

The PSD-Blob is also padded as needed with additional bytes to accommodate the needs of the checksum algorithm, as well as to add a further layer of security, if required, as indicated in a step 106. In the case of additional security requirements, the padding bit pattern can be retained by the data contributor and supplied only when sensitive and confidential data are later shared (as discussed below in greater detail).

After the checksum is calculated for each PSD-Blob in a step 108, the checksum is added to the PSD-Info document, as noted in a step 110. An exemplary PSD-Info document is shown in the following Table 2.

TABLE 2

| Record Export Checksum Info Export date: Apr. 25, 2004 | | |
|---|---|---|
| Tablename | Exported Field Nos. | |
| Tumor_Description | 1, 5, 9, 16, 17, 18 | |
| Tablename | ID Field #1 | ID Field #2 |
| Tumor_Description | Subject_ID | Tumor_No |

| Tablename | ID Field #1 | ID Field #2 | Checksum for Exported Fields |
|---|---|---|---|
| Tumor_Description | 251000 | 174000 | 81827828 |
| Tumor_Description | 275000 | 215000 | 1520154295 |
| Tumor_Description | 277000 | 218000 | 584311072 |
| Tumor_Description | 38000 | 224000 | 1094207930 |

The table includes:
  File type identification and date of export.
  The table(s) from which the data and their respective field numbers were supplied.

In this example, only Tumor_Description fields are shown. However, six fields are actually included in the PSD-Blobs and the checksum calculations, as follows: 1(Subject_ID), 5(Tumor_No), 9(Primary_site), 16(T Stage), 17(N Stage), and 18(M Stage). The internal identifiers, Subject_ID and Tumor_No, uniquely identify each record and are included in the checksum calculation.

The final steps for the data contributor involve generating a public-private encryption key pair using standard 128 bit Rivest, Shamir, and Adleman (RSA) algorithms or other suitable techniques, as indicated in a step 114. In public/private key encryption, a computer generates a paired encryption key and decryption key. Once a message is encrypted with the encryption key, the only way to decrypt the message is to use the paired decryption key. Even if the algorithm used to encrypt the message is known, having the encryption key does not help. In fact the designation of "encryption" and "decryption" keys is deceptive, since either key can be used in some schemes to successfully encrypt a message as long as its paired key is used to decrypt the message. To help distinguish between the actual roles in a key pair, the encryption key is called the "private" key and the decryption key is called the "public" key. The PSD-Info document is encrypted with the private key, in accord with a step 112. The private key is kept secret and retained by the data contributor, while in a step 116, the public key is sent to the data receiver through a communication channel separate from the PSD-Info document.

Upon receiving the encrypted PSD-Info document, the data receiver uses the supplied public encryption key to decrypt the document, as indicated in a step 118. The unique record identifiers, field numbers, and checksum information for the unsent data are saved for later comparison to any sensitive and confidential data received, in a step 120. By using the record identifiers, field identifiers, and checksum information, it is possible to prove that the submitted shared information are indeed actually derived from data collected for a specific patient, but the shared information does not include information that could be used otherwise to improperly identify the patient or violate the patient's privacy rights. The same approach can be used in connection with other types of data that relate to specific information that is not to be initially shared with a data recipient.

The fact that the public key can successfully decrypt the document proves that the data contributor with the private key sent the data, and not some third party posing as the data contributor. Use of the public key in this manner thus guarantees the identity of the data source, i.e., the data receiver knows where the data came from, and the data contributor cannot deny submitting the data. This step further guarantees that the comparisons done with the sensitive data in the future are correctly interpreted.

Comments on Data "Granularity"

The checksums are calculated on a combination of the unique identifiers and any included data fields. The checksum calculation will thus always depend on the combination of fields that were included in the PSD-Blob. If the agreement to share data ultimately will involve all the available data fields or a definitive subset of fields, then only one checksum per record needs to be calculated. For example, if there are 10 data fields in a data record and the two parties have agreed that ultimately they will share the sensitive data from fields 3-9, each record will only require a checksum result on a single PSD-Blob containing the unique identifiers and fields 3-9 in a defined order. However, if it is possible that the two parties might ultimately only agree on sharing another subset of the fields (e.g., 3-5 and 8), then checksum information will have to be exchanged on all possible combinations of shared fields or simply on each individual field separately.

It is this last special case, i.e., sharing of information on each individual separate field, which requires the use of special byte padding mentioned above. If, for example, a checksum were calculated on a single long integer field value, it would be possible by trying up to 4294967296 different combinations to ascertain the original long integer value using the checksum. Byte padding of the information in the field using a bit pattern known only to the data contributor will make this random guessing game as difficult as desired, based on the length of the padding and the algorithm used to generate it. When the parties have agreed to share a field of the data, the byte padding bit pattern for that field is supplied to help in the reconstruction of the PSD-Blob, as described in greater detail below.

Auditing the On-going Collection of Data

All database records have default values to designate non-entered data (e.g., the "Not Done" value). During the data collection phase when only PSD-Info documents are being exchanged, checksums can be calculated by the data recipient on PSD-Blobs consisting of the unique identifiers and default non-entered data values. The checksums for the default non-entered data values can be compared with the PSD-Info document checksums sent by the data contributor. If the checksums are different, then real values must have been entered in the data fields.

Maintaining a "Change" History and Auditing Altered Data

Any modifications of previously collected data for which PSD-Info documents have been exchanged will be immediately apparent to the data receiver when the actual data shared are compared with the original PSD-Info document. If previously collected data are modified by the data contributor, information about that modification must therefore be provided to the data receiver. The exchange of such information can be as simple as the data contributor informing the data receiver that the original data were changed, thereby invalidating the original PSD-Info document. In this case, a new PSD-Info document covering the modified data set must be generated and exchanged, before exchanging the actual modified data. In the case where a data receiver may need to track all changes to original data during a future audit, the original data must be archived, along with its associated PSD-Info document, providing a history for the changes. The archival of the original data and its associated PSD-Info document can be accomplished by sending the original data to the data receiver in a separately encrypted document for archiving purposes. The decryption key for this document is not shared at this time. The data receiver will maintain the encrypted copy of the original data without being able to access it, since the data receiver will not have the decryption key required to decrypt the data. At a future date when an audit of all changes needs to be completed, the decryption key for the encrypted original data document can be shared. The data receiver will then be able to use the original PSD-Info document to verify the original data.

Auditing Data at the Data Contributor's Site

In the case of on-going data collection, a trusted third party may ask to verify that the data and/or data information being shared actually exists and can be traced back to original records. The use of the unique identifiers for the data sharing process enable data to be traced back to its origin without the need to share otherwise confidential information like patient demographics or social security numbers that would violate the right to privacy of the patient.

Sharing of Sensitive Data and Data Verification

Figure 4:
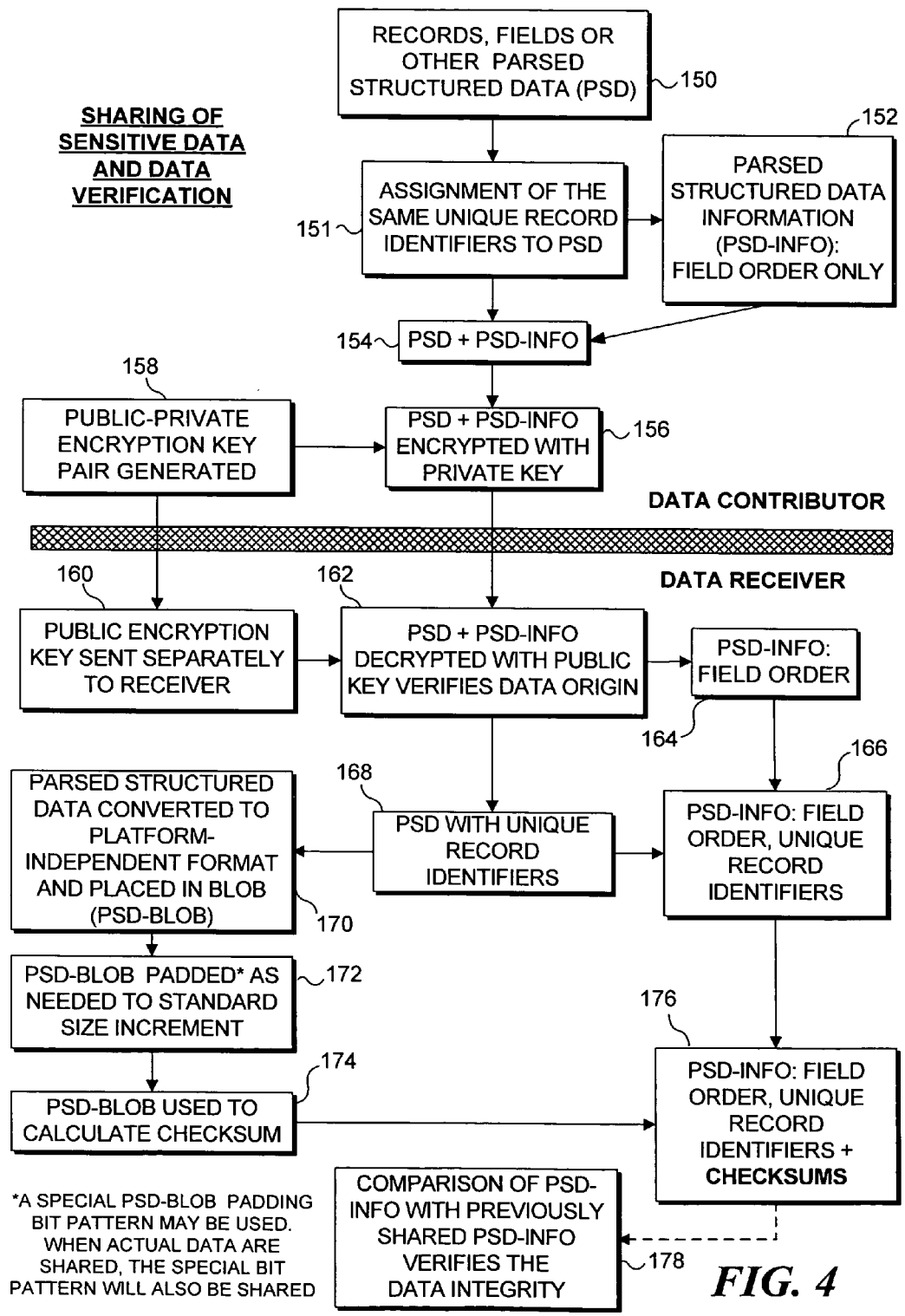
FIG. 4 is a flow chart showing the logical steps for sharing sensitive or confidential data and verifying the data, in accord with the present invention.

FIG. 4 shows that much the same steps used by the data contributor to prepare the PSD-Info document are employed by the data receiver to verify the sensitive data. The shared data include the unique identifiers and the field values used to create the original PSD-Info document.

When the sensitive data are sent, the data can be sent in any convenient format that makes the data easy to package and unpackage for placement in the appropriate fields by the data receiver. The PSD-Blob format, which is employed to pack field values together for calculation of checksums, can be used as a package format for the sensitive data that are encrypted and sent to the data receiver. In a step 150, the records, including the fields and other PSD to be sent are identified. A step 151 provides for assigning the same unique record identifiers to the PSD used during the "Sharing of Data 'Information' So As to Enable Future Verification" process described above. In a step 152, the field order information is added to the PSD-Info. In addition to the sensitive data, the information on the contained fields is sent in a PSD-Info document to guide the unpacking. A step 154 provides for combining the PSD and PSD-Info, so that in a step 156, the combination can be encrypted with a private key generated in a step 158. The public key portion of the public-private key is then sent to the data receiver in a step 160. In a step 162, the data receiver decrypts the PSD and PSD-Info with the public key, which ensures that the received encrypted sensitive data were sent by the party claiming to have sent them, for security as well as verification of data ownership. The PSD-Info defines the field order, as indicated in a step 164. In a step 168, the PSD with the unique record identifiers is recovered and the unique identifiers are added to the PSD-Info for later comparison in a step 166.

Once the sensitive data are received and decrypted, the data receiver creates its own PSD-Blob record from the unique identifiers and the sensitive data values in the field order specified in the PSD-Info, in a step 168. The PSD-Blob is then processed to create a platform-independent PSD-Blob version in a step 170, and any unique byte padding bit pattern obtained from the data contributor is added in a step 172. The processed PSD-Blob is then used to calculate the checksum in a step 174 and combined with the field order and unique record identifiers in a step 176. This checksum is then compared with the previously received PSD-Info document to verify that no changes have occurred in the data, in a step 178, which thus verifies the integrity of the data provided to the data receiver.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A computing device-implemented method used to enable verification of data integrity by a party with whom at least a part of the data are made available to be shared, wherein the data include the part of the data to be shared and any other part of the data that is not to be shared, and wherein the data are arranged in structured components, each structured component comprising a plurality of sub-components, the method comprising the steps of:
    (a) including at least two identifiers within each structured component of the data, if not already included, such that each unique identifier is assigned to a different subcomponent in the structured component of data;
    (b) processing the data to be shared with a polynomial expression to determine at least one descriptive value for each structured component of the data that will be made available to be shared, sharing of at least the part of the data occurring currently or at a subsequent time in a separate conveyance, said at least the part of the data being shared at a time when an entity having the data and the party agree to share said at least the part of the data;
    (c) producing data information that does not include the data that are to be made available to be shared, wherein the data information instead includes:
        (i) one item selected from the group consisting of:
            (A) an identification of the sub-components of the data to be shared; and
            (B) an order of the sub-components to be shared;
        (ii) said at least two unique identifiers assigned to the sub-components in the structured components of the data to be shared; and
        (iii) said at least one descriptive value for each structured component of the data to be shared;
    (d) encrypting the data information, producing encrypted data information;
    (e) conveying the encrypted data information to the party;
    (f) enabling the party to decrypt the encrypted data information to recover the data information; and
    (g) using only the decrypted data information for verifying the integrity of the data when the data are actually accessed by the party, without using a separate third party to aid in the verifying or the sharing of the data.

2. The method of claim 1, wherein the structured components are records, and the sub-components are fields.

3. The method of claim 1, wherein the descriptive value comprises a checksum.

4. The method of claim 1, wherein the step of determining at least one descriptive value comprises the step of determining a descriptive value for each sub-component of the data to be shared, producing a plurality of descriptive values that are included in the data information that is encrypted.

5. The method of claim 1, further comprising the steps of:
    (a) parsing the data, producing parsed structured data; and
    (b) converting the parsed structured data to a platform independent format.

6. The method of claim 5, further comprising the steps of:
    (a) padding the parsed structured data with a defined bit pattern; and
    (b) conveying the defined bit pattern to the party for use in subsequently verifying the integrity of data actually shared.

7. The method of claim 1, wherein the step of encrypting comprises the steps of:
    (a) providing a public key and a private key for encrypting the data information; and
    (b) separately conveying the public key to the party for use in decrypting the encrypted data information, so that if the encrypted data information is successfully decrypted with the public key, the party will have verified a source of the encrypted data information.

8. The method of claim 1, wherein for the case in which at least the portion of the data are to be shared currently with the data information,
    the step of encrypting the data information comprises the step of encrypting the data to be shared for inclusion with the data information, thereby producing encrypted shared data that includes both the data information and the data to be shared in an encrypted form, further comprising the steps of:
        (a) conveying the encrypted shared data to the party;
        (b) enabling the party to decrypt the encrypted shared data, recovering the data actually shared and the data information; and
        (c) verifying the integrity of the data that were actually shared when the data that have been shared are accessed by the party.

9. The method of claim 8, wherein the step of verifying the integrity of the data actually shared comprises the steps of:
    (a) determining at least one test descriptive value for each structured component of the data actually shared, by processing the data actually shared using the polynomial expression, for inclusion in test data information; and
    (b) comparing the test data information with the data information that was previously decrypted to determine if they are equal, thereby verifying the integrity of the data actually shared.

10. The method of claim 9, wherein the step of determining said at least one test descriptive value further comprises the steps of:
    (a) parsing the data that was actually shared, producing parsed conveyed structured data; and
    (b) converting the parsed conveyed structured data to a platform independent format.

11. The method of claim 10, wherein the step of determining said at least one test descriptive value further comprises the steps of:
(a) receiving a defined bit pattern that was used in padding the structured data; and
(b) padding the parsed conveyed structured data with the defined bit pattern.

12. The method of claim 1, wherein if the data to be shared are modified after the data information is produced and before sharing said data, further comprising the steps of:
(a) informing the party with whom at least part of the data are to be shared that the data have been modified; and
(b) providing new data information for the data to be shared that have been modified.

13. The method of claim 12, further comprising the step of providing an archival history of data modifications by:
(a) encrypting the data to be shared with an encryption key that is not initially provided to the party with whom at least part of the data are to be shared;
(b) conveying the data that were thus encrypted to the party; and
(c) storing the data that were encrypted with the data information for said data for subsequent decryption when a need arises for auditing changes made to the data that were encrypted.

14. The method of claim 1, wherein for the case in which at least the portion of the data are to be shared are currently not conveyed to the party when the encrypted data information is conveyed, further comprising the steps of:
(a) encrypting the at least the portion of the data to be shared, producing encrypted data to be shared;
(b) conveying the encrypted data to be shared to the party;
(c) enabling the party to decrypt the encrypted data to be shared, recovering the at least the portion of the data actually shared; and
(d) verifying the integrity of the at least the portion of the data actually shared using the data information that was previously decrypted.

15. A system for enabling verification of data integrity by a party with whom at least a part of the data are to be made available to be shared, wherein the data include the at least the part of the data to be shared and any portion of the data that is not to be shared, and wherein the data are arranged in structured components, each structured component comprising a plurality of sub-components, said system comprising:
(a) a memory in which machine instructions are stored;
(b) a data store comprising non-volatile storage for the data; and
(c) a processor that is coupled in communication with the memory and the data store, said processor executing the machine instructions stored in the memory, causing the processor to carry out a plurality of functions, including:
(i) including at least two unique identifiers within each structured component of the data, if not already included, such that each unique identifier is assigned to a different subcomponent in the structured component of data;
(ii) processing the data to be shared with a polynomial expression to determine at least one descriptive value for each structured component of the data that is to be made available to be shared, sharing of at least the part of the data occurring currently or at a subsequent time in a separate conveyance, said at least the part of the data being shared at a time when an entity having the data and the party agree to share said at least the part of the data;
(iii) producing data information that does not include the data to be subsequently shared, wherein the data information instead includes:
(A) one item selected from the group consisting of:
(1) an identification of the sub-components of the data to be shared; and
(2) an order of the sub-components to be shared;
(B) said at least two unique identifiers assigned to the sub-components in the structured components of the data to be shared; and
(C) said at least one descriptive value for each structured component of the data to be shared;
(iv) encrypting the data information, producing encrypted data information; and
(v) enabling the encrypted data information to be conveyed to the party, so that when decrypted by the party to recover the data information, the decrypted data information can be stored by the party for use in verifying the integrity of data at the time when the data are actually accessed by the party, without using a separate third party to aid in the verifying or the sharing of the data, and said verification taking place using only the decrypted data information.

16. The system of claim 15, wherein the structured components are records, and the sub-components are fields.

17. The system of claim 15, wherein the descriptive value comprises a checksum.

18. The system of claim 15, wherein the machine instructions further cause the processor to determine a descriptive value for each sub-component of the data to be shared, producing a plurality of descriptive values that are included in the data information that is encrypted.

19. The system of claim 15, wherein the machine instructions further cause the processor to:
(a) parse the data, producing parsed structured data; and
(b) convert the parsed structured data to a platform independent format.

20. The system of claim 19, wherein the machine instructions further cause the processor to pad the parsed structured data with a defined bit pattern.

21. The system of claim 15, wherein the processor encrypts the data information using a private key of a pair of public and private keys, the party having the public key for decrypting the encrypted data information.

22. The system of claim 15, wherein for the case in which at least the portion of the data are to be shared currently with the data information, the machine instructions further cause the processor to encrypt the data to be shared for inclusion with the data information, thereby producing encrypted shared data that include both the data information and the data to be shared in an encrypted form, and further cause the processor to convey the encrypted shared data to the party to enable the party to access the data actually shared and to verify the integrity of the data that was actually shared.

23. A computing device-implemented method for verifying an integrity of data that are subsequently to be made available to be received at another time from a contributor, wherein said data include at least a part of the data that is to be shared and any other part of the data that is not to be shared, and wherein the data are arranged in structured components, each structured component comprising a plurality of sub-components, comprising the steps of:
(a) receiving encrypted data information from the contributor;
(b) decrypting the encrypted data information to recover data information that does not include the data that are to be made available to be received at said another time, said data information including:
  (i) one item selected from the group consisting of:
    (A) an identification of the sub-components of the data to be shared; and
    (B) an order of the sub-components to be shared;
  (ii) at least two unique identifiers included within each structured component of the data to be shared, each unique identifier being assigned to a different sub-component in the structured component of the data; and
  (iii) at least one descriptive value for the data to be shared; and
(c) storing the decrypted data information for use in verifying the integrity of the data that are to be made available to be shared by the contributor at said another time, said sharing, if agreed to by the contributor and a recipient, taking place without aid of a separate third party, and verification taking place using only the decrypted data information and without aid of any separate third party.

24. The method of claim 23, wherein the structured components are records, and the sub-components are fields.

25. The method of claim 23, wherein the at least one descriptive value comprises a checksum.

26. The method of claim 23, wherein at said another time, further comprising the steps of:
  (a) receiving encrypted shared data from the contributor, said encrypted shared data including both the data actually shared and the data information;
  (b) decrypting the encrypted shared data, to recover the data actually shared and the data information; and
  (c) verifying the integrity of the data that were actually shared.

27. The method of claim 26, wherein the step of verifying the integrity of the data comprises the steps of:
  (a) determining at least one test descriptive value for each structured component of the data to be shared, by processing the data actually shared that were conveyed with a polynomial expression; and
  (b) comparing the at least one test descriptive value with each corresponding at least one descriptive value that was previously stored to determine if they are equal, and if so, indicating that the data are verified.

28. The method of claim 27, wherein the step of determining said at least one test descriptive value further comprises the steps of:
  (a) parsing the data that was shared, producing parsed conveyed structured data; and
  (b) converting the parsed conveyed structured data to a platform independent format.

29. The method of claim 28, wherein the step of determining said at least one test descriptive value further comprises the steps of:
  (a) receiving a defined bit pattern that was used in padding the structured data to produce the encrypted data that were received; and
  (b) padding the parsed conveyed structured data with the defined bit pattern.

30. The method of claim 27, wherein the step of determining at least one test descriptive value comprises the step of determining a test descriptive value for each sub-component of the data to be shared that was received from the contributor, producing a plurality of test descriptive values that are included in the data information that is encrypted.

31. The method of claim 23, wherein the step of decrypting the encrypted data includes the step of using a public key of a pair of public and private keys to decrypt the encrypted data received from the contributor, said private key of the pair of public and private keys having been used to encrypt the encrypted data.

32. The system of claim 15, wherein for the case in which at least the portion of the data are to be shared are currently not conveyed to the party when the encrypted data information is conveyed, the machine instructions further cause the processor to encrypt the data to be shared, thereby producing encrypted shared data that are conveyed to the party, the party using the data information that was decrypted to verify the integrity of the data that was actually shared.

33. A system for verifying an integrity of data that are to be received from a contributor at another time, wherein said data include at least a part of the data that is to be shared and any other part of the data that is not to be shared, and wherein the data are arranged in structured components, each structured component comprising a plurality of sub-components, said system comprising:
  (a) a memory in which machine instructions are stored;
  (b) a data store comprising non-volatile storage for the data; and
  (c) a processor that is coupled in communication with the memory and the data store, said processor executing the machine instructions stored in the memory, causing the processor to carry out a plurality of functions, including:
    (i) receiving encrypted data information from the contributor;
    (ii) decrypting the encrypted data to recover data information that does not include the data that are to be shared, said data information including:
      (A) one item selected from the group consisting of:
        (1) an identification of the sub-components of the data to be shared; and
        (2) an order of the sub-components to be shared;
      (B) at least two unique identifiers included within each structured component of the data to be shared, each unique identifier being assigned to a different subcomponent in the structured component of the data; and
      (C) at least one descriptive value for the data to be shared; and
    (iii) storing the decrypted data information in the non-volatile storage for use in verifying the integrity of the data that are to be made available to a recipient to be shared by the contributor, at said another time, said sharing, if agreed to by the contributor and the recipient, taking place without aid of a separate third party, and verification of the integrity of the data taking place using only the decrypted data information and without aid of any separate third party.

34. The system of claim 33, wherein the structured components are records, and the sub-components are fields.

35. The system of claim 33, wherein the at least one descriptive value comprises a checksum.

36. The system of claim 33, wherein at another time, the machine instructions further cause the processor to:
  (a) receive encrypted shared data from the contributor, said encrypted shared data including both the data actually shared and the data information;
  (b) decrypt the encrypted shared data, to recover the data actually shared and the data information; and
  (c) verify the integrity of the data that were actually shared.

37. The system of claim 36, wherein the machine instructions further cause the processor to verify the integrity of the data actually shared by:
  (a) determining at least one test descriptive value for each structured component of the data to be shared, by processing the data actually shared that were conveyed with a polynomial expression; and (b) comparing the at least one test descriptive value with each corresponding at least one descriptive value that was previously stored to determine if they are equal, and if so, indicating that the data are verified.

38. The system of claim 37, wherein the machine instructions further cause the processor to determine said at least one test descriptive value by:

(a) parsing the data that was actually shared, producing parsed conveyed structured data; and (b) converting the parsed conveyed structured data to a platform independent format.

39. The system of claim 38, wherein the machine instructions further cause the processor to determine said at least one test descriptive value by:

(a) receiving a defined bit pattern that was used in padding the structured data to produce the encrypted data that were previously received; and (b) padding the parsed conveyed structured data with the defined bit pattern.

40. The system of claim 37, wherein the machine instructions further cause the processor to determine said at least one test descriptive value by determining a test descriptive value for each sub-component of the data to be shared that was received from the contributor, producing a plurality of test descriptive values that are included in the data information that is encrypted.

41. The system of claim 33, wherein the machine instructions further cause the processor to employ a public key of a pair of public and private keys to decrypt the encrypted data received from the contributor, said private key of the pair of public and private keys having been used to encrypt the encrypted data.

42. A memory medium on which machine readable instructions are stored, which when executed by a computing device, cause a processor to carry out a plurality of functions, including:

(a) including at least two unique identifiers with each structured component of data that are to be made available to be shared, if not already included within the data, wherein the data include both the data that is to be shared and any other part of the data that is not to be shared, and wherein the data are arranged in structured components, each structured component comprising a plurality of sub-components, and each unique identifier being assigned to a different subcomponent in the structured component of the data;

(b) processing the data to be shared with a polynomial expression to determine at least one descriptive value for each structured component of the data that are to be made available to be shared, said at least the part of the data being shared at a time when an entity having the data and the party agree to share said at least the part of the data;

(c) producing data information that does not include the data available to be shared at the different time, wherein the data information instead includes:

(i) one item selected from the group consisting of:

(A) an identification of the sub-components of the data to be shared; and (B) an order of the sub-components to be shared;

(ii) said at least two unique identifiers assigned to the subcomponents in the structured components of the data to be shared; and (iii) said at least one descriptive value for each structured component of the data that are to be shared; and (d) encrypting the data information, producing encrypted data information that is conveyed to the party, to enable the party to decrypt the encrypted data information to recover the decrypted data information for use in verifying the integrity of the data when the data are actually accessed by the party, verification of the integrity of the data taking place using only the decrypted data information and without using a separate third party to aid in the verifying or the sharing of the data.

43. A memory medium on which machine readable instructions are stored for verifying an integrity of data that are subsequently to be made available to be received at another time from a contributor, wherein said data includes at least a part of the data that is to be shared and any other part of the data that is not to be shared, and wherein the machine instructions, when executed by a computing device of a contributor, cause a processor to carry out a plurality of functions, including:

(a) receiving encrypted data information from the contributor;

(b) decrypting the encrypted data information to recover data information that does not include data that have subsequently been made available to be shared after the data information were encrypted, said data information including:

(i) one item selected from the group consisting of:

(A) an identification of the sub-components of the data to be shared; and (B) an order of the sub-components to be shared;

(ii) at least two unique identifiers included within each structured component of the data to be shared, each unique identifier being assigned to a different sub-component in the structured component of the data; and (iii) at least one descriptive value for the data to be shared; and (c) storing the decrypted data information for use in verifying the integrity of the data when the data are subsequently accessed after being shared, said sharing occurring without aid from a separate third party, and verification of the integrity of the data taking place using only the decrypted data information and without aid from any separate third party.

44. A computing device-implemented method used to enable verification of data integrity by a party with whom at least a part of the data are made available to be shared, wherein the data include the part of the data to be shared and any other part of the data that is not to be shared, and wherein the data are arranged in structured components, each structured component comprising a plurality of sub-components, the method comprising the steps of:

(a) including at least two identifiers within each structured component of the data, if not already included, such that each identifier is assigned to a different subcomponent in the structured component of data, a combination of said at least two identifiers uniquely identifying each structure component;

(b) processing the data to be shared with a polynomial expression to determine at least one descriptive value for each structured component of the data that will be made available to be shared, sharing of at least the part of the data occurring currently or at a subsequent time in a separate conveyance, said at least the part of the data being shared at a time when an entity having the data and the party agree to share said at least the part of the data;

(c) producing data information that does not include the data that are to be made available to be shared, wherein the data information instead includes:
  (i) one item selected from the group consisting of:
    (A) an identification of the sub-components of the data to be shared; and
    (B) an order of the sub-components to be shared;
  (ii) said at least two unique identifiers assigned to the sub-components in the structured components of the data to be shared; and
  (iii) said at least one descriptive value for each structured component of the data to be shared;

(d) encrypting the data information, producing encrypted data information;

(e) conveying the encrypted data information to the party;

(f) enabling the party to decrypt the encrypted data information to recover the data information; and (g) using only the decrypted data information for verifying the integrity of the data when the data are actually accessed by the party, without using a separate third party to aid in the verifying or the sharing of the data.

* * * * *